United States Patent [19]

Knupfer et al.

[11] 4,284,787
[45] Aug. 18, 1981

[54] PROCESS FOR THE PREPARATION OF 1,2,3-TRIAZOLES SUBSTITUTED IN THE 2-POSITION

[75] Inventors: Hans Knupfer; Carl-Wolfgang Schellhammer, both of Bergisch-Gladbach, Fed. Rep. of Germany

[73] Assignee: Bayer Aktiengesellschaft, Leverkusen, Fed. Rep. of Germany

[21] Appl. No.: 29,049

[22] Filed: Apr. 11, 1979

[30] Foreign Application Priority Data

Apr. 13, 1978 [DE] Fed. Rep. of Germany ....... 2815956

[51] Int. Cl.$^3$ ................. C07D 209/04; C07D 209/06; C07D 401/04; C07D 405/04
[52] U.S. Cl. ............................. 548/256; 252/301.22; 252/301.24; 252/301.29; 542/455; 542/456; 542/458; 546/157; 546/276; 548/128; 548/178; 548/217; 548/224; 548/255; 548/257
[58] Field of Search .......... 260/308 A, 302 H, 307 D, 260/304 C; 546/157, 276; 542/455, 456; 548/256, 255, 128, 178, 162, 217, 222, 224, 257

[56] References Cited

PUBLICATIONS

Summers et al., J. Chem. Soc. (London), 1965, pp. 3312–3318.

Boulton et al., J. Chem. Soc. C., (London), 1967, pp. 2005–2007.

Primary Examiner—Alton D. Rollins
Attorney, Agent, or Firm—Sprung, Felfe, Horn, Lynch & Kramer

[57] ABSTRACT

Triazoles of the formula

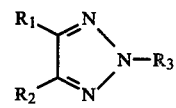

in which
  $R_1$ is hydrogen or a substituent of the type indicated in the description,
  $R_2$ is a substituent, or
  $R_1$ and $R_2$, together with the triazole ring carbon atoms to which they are bonded, form a carbocyclic or heterocyclic ring, and
  $R_3$ is the radical of an aromatic-carbocyclic or aromatic-heterocyclic system, are obtained in an elegant manner when compounds of the formula II are treated with a basic compound, preferably a tertiary amine. The triazoles are, inter alia, valuable starting materials for the preparation of optical brighteners.

4 Claims, No Drawings

PROCESS FOR THE PREPARATION OF 1,2,3-TRIAZOLES SUBSTITUTED IN THE 2-POSITION

The invention relates to a process for the preparation of 1,2,3-triazoles substituted in the 2-position, of the formula

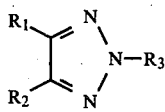 (I)

in which
- $R_1$ is hydrogen or a substituent,
- $R_2$ is a substituent, or
- $R_1$ and $R_2$, together with the triazole ring carbon atoms to which they are bonded, form a carbocyclic or heterocyclic ring, and
- $R_3$ is the radical of an aromatic-carbocyclic or aromatic-heterocyclic system.

The process is characterised in that compounds of the formula

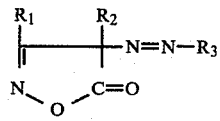 (II)

in which
$R_1$, $R_2$ and $R_3$ have the meaning indicated above, are treated with a basic compound Suitable substituents $R_1$ and $R_2$ are, in particular, alkyl, aralkyl, cycloalkyl, alkenyl, radicals of aromatic-carboxylic systems and of heterocyclic systems, in particular of aromatic-heterocyclic systems, and the carboxyl group and sulpho group and acid derivatives derived from these groups, such as esters and amides.

$R_1$ and $R_2$ preferably represent $C_1$-$C_{18}$-alkyl, which can be substituted, for example by —OH, halogen, such as Cl, Br and F, amino, radicals of primary and secondary amines, alkoxy, in particular $C_1$-$C_4$-alkoxy, cyano, carboxyl, carbalkoxy, optionally N-substituted carbamoyl, alkylsulphonyl or arylsulphonyl or optionally N-substituted sulphamoyl; cycloalkyl, in particular cyclohexyl and cyclopentyl; alkenyl, in particular vinyl, allyl and propenyl; aryl, such as phenyl, which can be substituted by halogen, alkyl, alkoxy, nitro, cyano, phenyl, carboxyl, sulpho, carbalkoxy, optionally N-substituted carbamoyl or optionally N-substituted sulphamoyl, sulphonic acid esters or acyl radicals, such as alkylcarbonyl or arylcarbonyl; optionally substituted naphthyl; aralkyl, such as optionally substituted benzyl; heterocyclic radicals, such as pyridyl or thienyl; or aralkyl, in particular optionally substituted benzyl radicals or phenylethyl radicals.

$R_1$ and $R_2$, together with the triazole ring carbon atoms to which they are bonded, can also form a heterocyclic or carbocyclic ring, for example a 5-membered or 6-membered carbocyclic ring.

Suitable substituents $R_3$ are, in addition to aromatic-carbocyclic radicals, such as optionally substituted phenyl or optionally substituted naphthyl, radicals of aromatic-heterocyclic systems, such as pyridyl or coumarin-7-yl, which can preferably contain further substituents in the 3-position, preferably aryl, such as optionally substituted phenyl and optionally substituted naphthyl, or alkoxycarbonyl or aromatic-heterocyclic radicals, such as triazolyl, such as, for example, 1,2,4-triazol-1-yl, 1,2,3-triazol-1-yl or 1,2,3-triazol-2-yl, it being possible for the triazolyl radicals to carry further substituents or fused-on rings. Examples of triazolyl radicals substituted in this manner are 3- and/or 5-alkyl-, aryl- and aralkyl-1,2,4-triazol-1-yl; 4- and/or 5-alkyl, aryl- or aralkyl-1,2,3-triazol-1-yl or -triazol-2-yl, it also being possible for the radicals in the 4-position and 5-position to form, together, the remaining members of a fused-on carbocyclic ring, such as, for example, of a benzene ring or naphthalene ring; pyrazolyl, such as pyrazol-1-yl and substituted pyrazol-1-yl, possible substituents being, in particular, halogen, preferably chlorine, alkyl, aryl and aralkyl, and these substituents preferably being in the 4-position of the hydrazol-1-yl radical; thien-2-yl; carbostyril-7-yl; benztriazol-5-yl substituted in the 2-position, such as 2-styrylbenztriazol-5-yl; 1,2,4-thiadiazol-3-yl substituted in the 5-position, such as 5-phenyl-1,2,4-thiadiazolyl; 2-methyl-benzoxazol-5-yl or -6-yl and -benzthiazol-5-yl or 6.

Suitable basic compounds are, in particular, nitrogen bases, such as amines, in particular tertiary amines and bis-tertiary diamines, such as trialkylamines and dialkylarylamines, which can be further substituted. Trialkylamines with 1 to 6 C atoms per alkyl radical, which can be substituted, for example by hydroxyl or ethoxy, may be mentioned in particular. Alkali metal carbonates and alkaline earth metal carbonates may also be mentioned as suitable basic compounds.

The basic compounds are employed in this process in amounts of about 0.01–10 mols, relative to 1 mol of the compound (II).

The reaction temperature depends on the nature of the compound (II) employed and in general is between about 20° C. and about 150° C., preferably between 60° and 120° C.

The reaction is appropriately carried out in a diluent. Examples of suitable diluents are the abovementioned tertiary amines, and also alcohols, in particular secondary aliphatic alcohols, such as isopropanol or isobutanol, or aminoalcohols, such as 1-dimethylaminopropanol.

Some of the starting compounds (II) are known from the literature, for example the compound of the formula

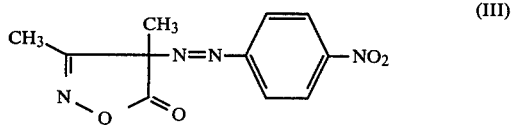 (III)

is known from Chem. Pharm. Bull. (Tokyo) 12, 1,021 (1969) and the compound

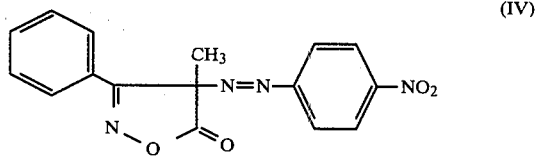 (IV)

is known from Soc. 1965, 5,414.

The compound (IV) is obtained by reacting p-nitrophenyldiazonium chloride with 3-phenyl-4-methyl-isoxazolin-5-one.

The compounds (II) of the present Application are also obtained by this process, from the corresponding diazonium salts $$[R_3-N_2]^{\oplus}X^{\ominus} \quad (V)$$

wherein $X^{\ominus}$ represents an anion, in particular $Cl^{\ominus}$ or $SO_4^{2\ominus}$, and the isoxazolin-5-one compounds of the formula

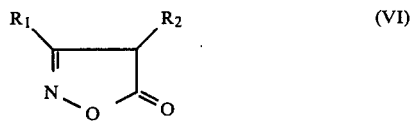

(VI)

Suitable diazonium salts (V) are, in particular, those which are derived from the following amines: aniline; anilines which are substituted by one or more methyl groups with preferably 1–3 C atoms, alkenyl groups, aralkylene groups, nitro groups, halogen atoms, for example F, Cl or Br, cyano groups, carboxyl groups or derivatives thereof, sulphonic acid groups or derivatives thereof, alkylsulphonyl or arylsulphonyl groups, alkoxy or aryloxy groups, aralkyl groups, aryl groups, amino groups, alkylamino groups, dialkylamino groups and/or acylamino groups; appropriately substituted naphthyl-1-amines or -2-amines; phenanthrylamines or anthranylamines; pyrenylamines; 4,4′-diaminostilbene, which optionally carries further substituents, in particular sulpho, sulphamoyl, carboxyl, alkoxycarbonyl or cyano; aminopyridines, 2-aminobenzothiazole or 3-amino-5-phenyl-1,2,4-thiadiazole; 5-aminobenzotriazole; or 4-amino-naphthalimides which are substituted on the imide nitrogen by alkyl, aralkyl, alkenyl or aryl radicals which are optionally further substituted.

5-Amino-2-styryl-benzoxazoles, which are optionally further substituted in the styryl radical; 6-amino-2-styryl-benzoxazoles, which are optionally further substituted in the styryl radical; 5-amino-benzothiazoles, which are substituted in the 2-position by alkyl radicals or by styryl radicals which are optionally further substituted; 6-amino-2-styryl-benzothiazoles, which are optionally further substituted in the styryl radical; 5-amino-2-styryl-benzotriazoles, which are optionally further substituted in the styryl radical; 2-p-amino-styryl-benzoxazoles, which are optionally further substituted in the benzo nucleus of the benzoxazole; 2-p-amino-styryl-benzothiazoles, which are optionally further substituted in the benzo nucleus of the benzothiazole; 2-p-amino-styryl-benzotriazoles, which are optionally further substituted in the benzo nucleus of the benzotriazole; 2-p-amino-styrylnaphthothiazoles; 2-p-amino-styryl-naphthotriazoles; 6-amino-benzofuranes, which are optionally further substituted in the 2-position; 2-p-aminophenyl-benzofurane, 7-amino-3-phenylphenoxathiazine 2,2-dioxide or 3-aryl-7-amino-carbostyrils; 3-(p-aminophenyl)-carbostyril or 7-aminocoumarincarboxylic acid 3-alkyl esters; 7-aminocoumarin, which is optionally further substituted, preferably in the 3-position and preferably by aryl, such as optionally substituted phenyl and optionally substituted naphthyl, or aromatic-heterocyclic radicals, such as triazolyl, for example 1,2,4-triazol-1-yl, 1,2,3-triazol-1-yl or 1,2,3-triazol-2-yl, it being possible for these radicals to contain further substituents or fused-on rings.

Examples of substituted triazolyl radicals of this type are 3- and/or 5-alkyl-, -aryl- or -aralkyl-1,2,4-triazol-1-yl, 4- and/or 5-alkyl-, -aryl- or -aralkyl-1,2,3-triazol-1-yl or -triazol-2-yl, it also being possible for the radicals in the 4-position and 5-position to form, together, the remaining members of a fused-on carbocyclic ring, such as, for example, of an optionally substituted benzene ring or optionally substituted naphthalene ring.

Pyrazolyl, such as pyrazol-1-yl, and substituted pyrazolyl, possible substituents being, in particular, halogen, preferably chlorine, alkyl, aryl or aralkyl, these substituents preferably being in the 4-position, and thien-2-yl.

Examples of suitable isoxazolin-5-ones are 4-methyl-i (i=isoxazolin-5-one), 3,4-dimethyl-i, 4-β-hydroxyethyl-i, 3-methyl-4-ethyl-i, 3-methyl-4-β-hydroxyethyl-i, 4-γ-aminopropyl-i, 3-cyclopropyl-4-methyl-i, 3,4-diethyl-i, 3-methyl-4-isopropyl-i, 3-methyl-4-tert.-butyl-i, 3-propyl-4-ethyl-i, 3-methyl-4-ethyl-i, 3-methyl-4-(2-methyl-2-hydroxypropyl)-i, 4-phenyl-i, 3-methyl-4-cyclopentyl-i, 3-methyl-4-phenyl-i, 3-phenyl-4-methyl-i, 3-butyl-4-propyl-i, 3-p-bromophenyl-4-β-hydroxyethyl-i, 3-p-chlorophenyl-4-β-hydroxyethyl-i, 3-p-nitrophenyl-4-β-hydroxyethyl-i, 3-ethyl-4-phenyl-i, 3-phenyl-4-ethyl-i, 3-methyl-4-benzyl-i, 3-p-tolyl-4-β-hydroxyethyl-i, 3-tert.-butyl-4-phenyl-i, 3-methyl-4-(1-phenylpropyl)-i, 3-phenyl-4-(4-pyridyl)-i, 3-phenyl-4-(3-pyridyl)-i, 3-(3,4,5-trimethoxyphenyl)-4-β-hydroxyethyl-i, 3-phenyl-4-(2-chlorophenyl)-i, 3,4-diphenyl-i, 3-methyl-4-benzyl-i, 3-p-methoxyphenyl-4-methyl-i, 3-p-chlorophenyl-4-methyl-i, 3-biphenyl-4-methyl-i, 3,4-tetramethylene-i and 3,4-trimethylene-i.

Most of the isoxazolines mentioned are known from the literature. Where this is not the case, they can be obtained analogously to known isoxazolines from the corresponding starting compounds.

Most of the triazoles (I) are known. They are used, for example, as optical brighteners.

PREPARATION EXAMPLES FOR THE AZO COMPOUNDS

A. 23.7 g (0.1 mol) of 7-amino-3-phenyl-coumarin are dissolved in 240 ml of concentrated sulphuric acid at a maximum temperature of 30° C. The solution is cooled to 10° C. and the amine is diazotised with 32 g (0.106 mol) of nitrosylsulphuric acid. After 2 hours, the mixture is discharged onto ice and the diazonium salt is filtered off. 17.5 g (0.1 mol) of 3-phenyl-4-methyl-isoxazolin-5-one are dissolved in 150 ml of glacial acetic acid. 30 g of crystalline sodium acetate are added and the paste of the diazonium salt prepared above is introduced at 16° C. or below. The next day, the yellow azo compound is filtered off, washed with water and dried at 50° C. Yield: 41 g. A sample recrystallised from benzene/light petrol melts at 134° C., with decomposition.

B. 18 g (0.1 mol) of 5-amino-3-phenyl-1,2,4-triadiazole are dissolved in 300 ml of 85% strength phosphoric acid. After leaving the solution to stand overnight, 100 ml of glacial acetic acid are added and the amine is diazotised with 32 g (0.106 mol) of nitrosylsulphuric acid at 0° C. to −2° C. in the course of 3 hours. After leaving the mixture to stand at −5° C. for 25 hours, a solution of 19.3 g (0.11 mol) of 3-phenyl-4-methyl-isoxazolin-5-one in 150 ml of glacial acetic acid is added dropwise in the course of 25 minutes and the mixture is subsequently stirred for 1 hour. It is discharged onto ice-water and the yellow azo compound is filtered off and, after washing with water, dried. Yield: 35.5 g. A sample undissolved from benzene melts at 118° C., with decomposition.

C. 14.3 g. (0.054 mol) of 7-amino-1-ethyl-3-phenylcarbostyril are dissolved in 150 ml of hot glacial acetic acid. 20 ml of concentrated hydrochloric acid are added to the solution and the mixture is cooled to 0° C. The amine is diazotised with a solution of 3.8 g (0.055 mol) of sodium nitrite in 10 ml of water at 0°-5° C. After 2 hours, a solution of 15 g (0.059 mol) of 3-p-biphenylyl-4-methyl-isoxazolin-5-one in 150 ml of glacial acetic acid is added to the solution of the diazonium salt. The yellow azo compound is filtered off the next day, washed with water and dried. Yield: 27.5 g, melting point: 111°-112° C., with decomposition.

EXAMPLES OF REARRANGEMENT REACTIONS TO GIVE THE V-TRIAZOLE COMPOUND

A. 26.5 g of 3-phenyl-4-methyl-isoxazolin-5-one-4-azo-4-nitrobenzene (crude material) are dissolved in 120 ml of methylene chloride; the solution is clarified with Tonsil and then added dropwise to a mixture, warmed to 70° C., of 200 ml of triethylamine and 200 ml of isopropanol. The methylene chloride is thereby distilled off continuously. The mixture is then boiled under reflux for a further 3 hours and cooled to +10° C. and the 2-p-nitrophenyl-4-methyl-5-phenyl-1,2,3-triazole is filtered off. Yield: 7.1 g, melting point: 160°-164° C.

B. 27.7 g of 3-phenyl-4-benzyl-isoxazolin-5-one-4-azo-7-(3-p-chlorophenyl)-coumarin are suspended in 175 ml of xylene and the suspension is added to 150 ml of 1-dimethylamino-propan-2-ol, warmed to 110° C., in the course of 5 minutes. The mixture is then boiled under reflux for a further half an hour, the contents of the flask are concentrated down to 75 ml by applying a vacuum and 200 ml of methanol are added. The product which has separated out is filtered off and dried. Yield: 17.5 g, melting point: 198°-200° C. After recrystallising from glycol monomethyl ether-acetate, 12.6 g of pale yellow crystals of melting point 199°-202° C. are obtained.

The compounds listed in the table are prepared analogously to the above examples.

| No. | $R_1$ | $R_2$ | $R_3$ | Azo compound Process | Melting point (°C.) Decomposition | Triazole compound Process | Melting point (°C.) |
|---|---|---|---|---|---|---|---|
| 1 | —$CH_3$ | —$CH_2$—$C_6H_5$ | —C₆H₄—CH=CH—N(benzotriazolyl) | C | 134 | B | 187–189 |
| 2 | —$C_6H_5$ | —$CH_3$ | " | C | 132 | B | 200–203 |
| 3 | —$C_6H_5$ | —$CH_3$ | (methylcoumarin-phenyl) | A | 124 | A,B | 164–165 |
| 4 | —$CH_3$ | —$CH_2$—$C_6H_5$ | " | A | 133 | B | 170–171 |
| 5 | —$CH_3$ | —$C_6H_5$ | " | A | 97–102 | A | 164–165 |
| 6 | —$C_6H_5$ | —$CH_2$—$C_6H_5$ | " | A | 118–119 | B | 173–175 |
| 7 | —C₆H₄—$OCH_3$ | —$CH_3$ | " | A | 103–111 | B | 176–179 |
| 8 | —C₆H₄—Cl | —$CH_3$ | " | A | 125–126 | B | 181–184 |
| 9 | —$C_6H_5$ | —$CH_2$—$C_6H_5$ | " | B | 128–130 | B | 199–202 |
| 10 | —$C_6H_5$ | —$C_6H_5$ | " | B | 104–106 | B | 247–248 |
| 11 | —$C_6H_5$ | —$CH_3$ | " | B | 113–114 | B | 246–248 |
| 12 | —$C_6H_5$ | —$C_6H_5$ | (dichlorophenyl-methylcoumarin) | B | 81 | B | 200–203 |
| 13 | —$C_6H_5$ | —$CH_3$ | " | A | 124 | A | 239–241 |
| 14 | —$CH_3$ | —$CH_2$—$C_6H_5$ | (chloropyrimidyl-methylcoumarin) | A | 132 | A,B | 201–202 |
| 15 | —C₆H₄—C₆H₅ | —$CH_3$ | " | A | 126–128 | A | 287–288 |
| 16 | —$C_6H_5$ | —$CH_2$—$C_6H_5$ | " | A | 139–140 | B | 172–175 |
| 17 | —C₆H₄—$OCH_3$ | —$CH_3$ | " | A | 125–127 | B | 251–253 |

-continued $$\underset{N}{\overset{R_1}{\underset{O}{\bigvee}}}\overset{R_2}{\underset{O}{\bigvee}} + X[N_2-R_3] \longrightarrow \underset{N}{\overset{R_1}{\underset{O}{\bigvee}}}\overset{R_2}{\underset{O}{\overset{N=N-R_3}{\bigvee}}} \longrightarrow \underset{R_2}{\overset{R_1}{\bigvee}}\overset{N}{\underset{N}{\overset{N}{\bigvee}}}N-R_3$$

| | | | | Azo compound | | Triazole compound | |
|---|---|---|---|---|---|---|---|
| No. | $R_1$ | $R_2$ | $R_3$ | Process | Melting point (°C.) Decomposition | Process | Melting point (°C.) |
| 18 |  —⟨⟩—Cl | —CH$_3$ | " | A | 114–115 | B | 254–257 |
| 19 | 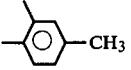 CH$_3$, CH$_3$ | —CH$_3$ | " | A | 63 | A | 207–209 |
| 20 | 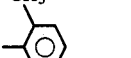 CH$_3$, CH$_3$ | —CH$_3$ | " | A | 63 | A | 205–206 |
| 21 | —C$_6$H$_5$ | —CH$_3$ | 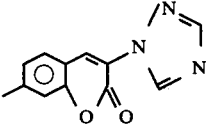 | C | 123 | A | 236–237 |
| 22 | —CH$_3$ | —CH$_2$—C$_6$H$_5$ | " | C | — | A | 202–203 |
| 23 | —C$_6$H$_5$ | —CH$_2$—C$_6$H$_5$ | " | C | 65–70 | B | 185–186 |
| 24 | 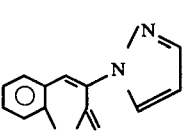 —⟨⟩—OCH$_3$ | —CH$_3$ | 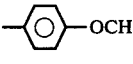 | A | 117–118 | B | 220–222 |
| 25 | 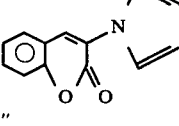 —⟨⟩—Cl | —CH$_3$ | " | A | 117–118 | B | 229–231 |
| 26 | —CH$_3$ | —CH$_2$—C$_6$H$_5$ |  | C | 103–107 | A | 194–195 |
| 27 | —C$_6$H$_5$ | —CH$_3$ | 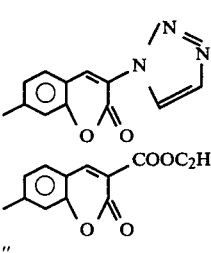 | C | 110 | B | 182 |
| 28 | —C$_6$H$_5$ | —CH$_2$—C$_6$H$_5$ | " | C | 114–115 | B | 151–152 |
| 29 | —C$_6$H$_5$ | —CH$_2$—C$_6$H$_5$ | 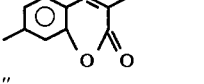 | C | 131–133 | B | 233–234,5 |
| 30 | —C$_6$H$_5$ | —CH$_3$ | 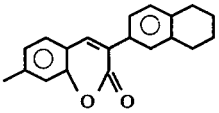 | C | 100 | A | 161–165 |
| 31 | —C$_6$H$_5$ | —CH$_3$ | 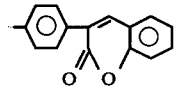 | C | 120 | A | 151–153 |
| 32 | 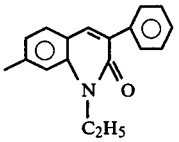 —⟨⟩—⟨⟩ | —CH$_3$ | 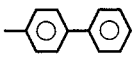 | C | 111–112 | A | 202–203 |

-continued $$\underset{\substack{R_1\\ \diagdown\\ N\\ \diagdown\\ O}}{\overset{R_2}{\diagdown}}\!\!\!\!\!\!\!\!\!\overset{}{\underset{O}{\diagdown}}\ +\ X[N_2\!-\!R_3]\ \longrightarrow\ \underset{\substack{R_1\\ \diagdown\\ N\\ \diagdown\\ O}}{\overset{R_2}{\diagdown}}\!\!\!\!\!\!\!\!\!\overset{N=N-R_3}{\underset{O}{\diagdown}}\ \longrightarrow\ \underset{\substack{R_2\\ \diagdown\\ N}}{\overset{R_1}{\diagdown}}\!\!\!\!\!\!\!\overset{N}{\underset{N}{\diagdown}}\!\!\!\!\!\overset{}{\underset{}{\diagup}}N-R_3$$

| | | | | Azo compound | | Triazole compound | |
|---|---|---|---|---|---|---|---|
| No. | R₁ | R₂ | R₃ | Process | Melting point (°C.) Decomposition | Process | Melting point (°C.) |
| 33 | —C₆H₅ | —CH₃ | [tolyl-SO₂-O-CH=C-C₆H₅] | C | 110 | B | 140–142 |
| 34 | —C₆H₅ | —CH₃ | [tolyl-O-CH=C-tolyl] | C | 115–116 | B | 176–178 |
| 35 | —C₆H₅ | —CH₃ | [methylnaphthyl-NO₂] | C | 108 | A | 120–122 |
| 36 | —C₆H₅ | —CH₃ | [dimethylphenyl-N=C(CH₃)-O] | C | — | A | 130–132 |
| 37 | —C₆H₅ | —CH₃ | [C₆H₅-C(=N-N=C(CH₃)-S) ring] | B | 118 | A | 138–139 |
| 38 | —C₆H₅ | —CH₃ | [dimethylphenyl-N=C(CH₃)-S] | C | — | A | 103–105 |
| 39 | —C₆H₅ | —CH₃ | [methylphenyl-N(N=)N-CH=CH-C₆H₅] | C | 70 | B | 143–146 |
| 40 | $\underset{}{\underset{}{\text{—}\!\bigcirc\!\text{—CN}}}$ | —CH₃ | " | C | 105–110 | B | 240–243 |
| 41 | —CH₃ | —CH₂—C₆H₅ | " | C | 117–119 | B | 136–137 |
| 42 | —C₆H₅ | —CH₃ | [dimethylphenyl-N=C(-CH=CH-C₆H₅)-O] | C | 69 | A | 186–187 |
| 43 | —C₆H₅ | —CH₃ | [dimethylphenyl-N=C(-CH=CH-C₆H₅)-O] | C | 75–79 | A | 163–164,5 |
| 44 | —C₆H₅ | —CH₃ | [dimethylphenyl-N=C(-CH=CH-C₆H₄Cl)-O] | C | 90–94 | A | 219–221 |
| 45 | —C₆H₅ | —CH₃ | [dimethylphenyl-N=C(-CH=CH-C₆H₄Cl)-O] | C | 114–116 | A | 196–197 |
| 46 | —C₆H₅ | —CH₃ | [dimethylphenyl-N=C(-CH=CH-C₆H₃Cl₂)-O] | C | 93–101 | A | 185 |

-continued

| No. | R₁ | R₂ | R₃ | Azo compound Process | Melting point (°C.) Decomposition | Triazole compound Process | Melting point (°C.) |
|---|---|---|---|---|---|---|---|
| 47 | —C₆H₅ | —CH₃ | (benzoxazole)-CH=CH-(2,6-dichlorophenyl) | C | 114–115 | A | 216–219 |
| 48 | —CH₃ | —CH₂—C₆H₅ | (benzoxazole)-CH=CH-(4-chlorophenyl) | C | 116–118 | B | 202 |
| 49 | —CH₃ | —CH₂—C₆H₅ | (benzoxazole)-CH=CH-(4-chlorophenyl) | C | 115–123 | A | 181–183 |
| 50 | —C₆H₅ | —CH₂—C₆H₅ | (benzoxazole)-CH=CH-(4-chlorophenyl) | C | 99–105 | B | 176–178 |
| 51 | —CH₃ | —CH₂—C₆H₅ | (4-substituted phenyl)-CH=CH-(benzoxazole) | C | 101–105 | A | 175–178 |
| 52 | —C₆H₅ | —CH₃ | (benzothiazole)-CH=CH-C₆H₅ | C | 65–72 | A | 173–175 |
| 53 | —C₅H₅ | —CH₃ | (benzothiazole)-CH=CH-(4-chlorophenyl) | C | 99–102 | A | 216–218 |
| 54 | —CH₃ | —CH₂—C₆H₅ | (benzothiazole)-CH=CH-(4-chlorophenyl) | C | 109–111 | A | 179–181 |
| 55 | —C₆H₅ | —CH₃ | (benzothiazole)-CH=CH-(2,6-dichlorophenyl) | C | 103–105 | A | 224–226 |
| 56 | —CH₃ | —CH₂—C₆H₅ | (benzothiazole)-CH=CH-(4-chlorophenyl) | C | 126 | A | 187–189 |
| 57 | -C₆H₄-Cl | —CH₃ | (benzothiazole)-CH=CH-(4-chlorophenyl) | C | 110–112 | B | 262–265 |
| 58 | -C₆H₄-OCH₃ | —CH₃ | (benzothiazole)-CH=CH-(4-chlorophenyl) | C | 125–126 | B | 219–223 |
| 59 | —C₆H₅ | —CH₂—C₆H₅ | (benzothiazole)-CH=CH-(4-chlorophenyl) | C | 102–108 | B | 190–192 |

-continued

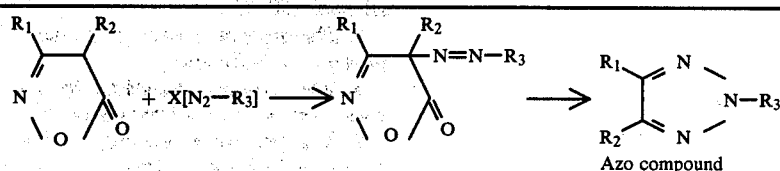

| No. | R₁ | R₂ | R₃ | Process | Azo compound Melting point (°C.) Decomposition | Process | Triazole compound Melting point (°C.) |
|---|---|---|---|---|---|---|---|
| 60 | biphenyl | —CH₃ | 2-styryl-benzthiazole (Cl-substituted) | C | 68–79 | B | 233–234 |
| 61 | 4-Cl-phenyl | —CH₃ | 2-styryl-benzthiazole (Cl-substituted) | C | 110–118 | B | 290–292 |
| 62 | —C₆H₅ | —C₆H₅ | 2-styryl-benzthiazole | C | 83–84 | B | 206–208 |
| 63 | —C₆H₅ | —CH₃ | 2-(naphth-benzoxazolyl)-phenyl | C | 119–120 | A | 206–207 |
| 64 | biphenyl | —CH₃ | 2-(naphth-benzoxazolyl)-phenyl | C | 105 | B | 252–255 |
| 65 | —C₆H₅ | —CH₃ | 2-(naphth-benzoxazolyl)-biphenyl | C | 121 | B | 226–227 |
| 66 | —C₆H₅ | —CH₂—C₆H₅ | " | C | 131–132 | B | 174–176 |
| 67 | 4-Cl-phenyl | —CH₃ | " | C | 123–125 | B | 245–246 |
| 68 | —C₆H₅ | —C₆H₅ | " | C | 99–101 | B | 238–241 |
| 69 | —CH₃ | —CH₂—phenyl | " | C | 124–125 | B | 235–236 |

We claim:

1. A process for the preparation of a compound of the formula

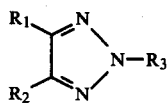

wherein

R₁ and R₂ each independently is C₁–C₁₈-alkyl; C₁–C₁₈-alkyl substituted by —OH, halogen, amino, C₁–C₄-alkoxy, cyano, carboxyl, carbalkoxy, carbamoyl; alkylsulphonyl or arylsulphonyl or sulphamoyl; cyclohexyl; cyclopentyl; vinyl; allyl; propenyl; phenyl; phenyl substituted by halogen, alkyl, alkoxy, nitro, cyano, phenyl, carboxyl, sulpho, carbalkoxy, carbamoyl, sulphamoyl, sulphonic acid esters, alkylcarbonyl or arylcarbonyl; naphthyl; pyridyl; thienyl; or benzyl radicals or phenylethyl radicals, or R₁ and R₂, together with the triazole ring carbon atoms to which they are bonded, can also form 5-membered or 6-membered carbocyclic ring, and R₃ is phenyl; naphthyl; pyridyl or coumarin-7-yl optionally substituted by phenyl, by naphthyl, by alkoxycarbonyl or by 1,2,4-triazol-1-yl, 1,2,3-triazol-1-yl or 1,2,3-triazol-2-yl, it being possible for the triazolyl radicals to carry 5-alkyl-, aryl- and aralkylsubstituents, it also being possible for the radicals in the 4-position and 5-position to form, together, the remaining members of a fused-on benzene ring or naphthalene ring; pyrazolyl; pyrazolyl substituted by halogen, alkyl, aryl and aralkyl; thien-2-yl; carbostyril-7-yl; 2-styrylbenztriazol-5-yl; 5-phenyl-1,2,4-thiadiazolyl; 2-methyl or styryl-benzoxazol-5-yl or -6-yl and 2-methyl or styrylbenzthiazol-5-yl or -6-yl, comprising contacting a compound of the formula

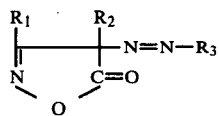
with a basic compound at a temperature between about 20° and 150° C.
2. The process according to claim 1, conducted in the presence of a diluent.
3. The process according to claim 1, wherein the basic compound is a tertiary amine.
4. The process according to claim 1, wherein $R_3$ is coumarin-7-yl optionally substituted as indicated.
* * * * *